United States Patent [19]

Bates et al.

[11] Patent Number: 5,270,307

[45] Date of Patent: Dec. 14, 1993

[54] PYRROLO(1,2-B)-(1,2)-BENZOTHIAZIN-10-ONE AND ITS USE AS AN ANTIMICROBIAL

[75] Inventors: Dallas K. Bates; Kelley A. Tafel, both of Houghton, Mich.

[73] Assignee: The Dow Chemical Company, Midland, Mich.

[21] Appl. No.: 37,960

[22] Filed: Mar. 26, 1993

[51] Int. Cl.$^5$ .................... C07D 279/02; A01N 43/58
[52] U.S. Cl. .................... 514/224.5; 544/33
[58] Field of Search .................... 544/33; 514/224.5

[56] References Cited

U.S. PATENT DOCUMENTS 3,492,299 1/1970 Rasmussen .................... 260/243

OTHER PUBLICATIONS

K. C. Nicolaou et al., *J. Org. Chem.*, 1985, 50. pp. 1440–1456.

S. Oae and T. Numata, *Tetrahedron*, 1974, 30, 2641–2646.

*Primary Examiner*—John M. Ford
*Attorney, Agent, or Firm*—S. Preston Jones; Ronald G. Brookens

[57] ABSTRACT

Pyrrolo-(1,2-b)-(1,2)-benzothiazin-10-one is prepared which corresponds to the formula:

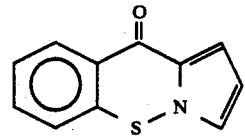

This compound has been found to exhibit antimicrobial activity in industrial and commercial applications and compositions containing this compound are so employed.

5 Claims, No Drawings

PYRROLO(1,2-B)-(1,2)-BENZOTHIAZIN-10-ONE AND ITS USE AS AN ANTIMICROBIAL

BACKGROUND OF THE INVENTION

This invention relates to the compound pyrrolo-(1,2-b)-(1,2)-benzothiazin-10-one and its use as an antimicrobial agent.

U.S. Pat. No. 3,492,299 discloses the preparation of compounds of the formula:

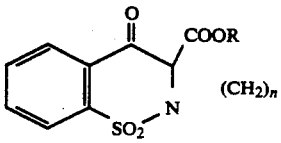

wherein R is ethyl and n is 2 or 3. These compounds are disclosed as being useful as ultra-violet light absorbers.

The desirability of identifying or discovering new antimicrobial agents is widely recognized. New antimicrobial agents are desired for several reasons; these include, but are not limited to, responding to the problem created by the development of microbe strains resistant to known antimicrobials, the occurrence of undesirable interactions of certain known antimicrobials with the medium or product in which the antimicrobial is used, and high toxicity of certain known antimicrobials to certain non-target organisms such as mammals.

The present invention solves these problems by disclosing a new compound which may be employed as an antimicrobial.

SUMMARY OF THE INVENTION

The present invention is directed to the compound pyrrolo-(1,2-b)-(1,2)-benzothiazin-10-one which corresponds to the formula:

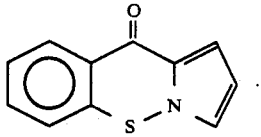

I

The present invention is also directed to an antimicrobial composition comprising an antimicrobially-effective amount of the compound pyrrolo-(1,2-b)-(1,2)-benzothiazin-10-one, as the active material, in intimate admixture with an inert diluent.

The present invention is further directed to a method for inhibiting microorganisms in a microbial habitat which comprises contacting said microbial habitat with an antimicrobial composition comprising an antimicrobially-effective amount of the compound pyrrolo-(1,2-b)-(1,2)-benzothiazin-10-one, as the active material, in intimate admixture with an inert diluent.

In addition, the present invention is directed to the use of pyrrolo-(1,2-b)-(1,2)-benzothiazin-10-one as a microorganism inhibitor.

DETAILED DESCRIPTION OF THE INVENTION

The compound of the present invention, pyrrolo-(1,2-b)-(1,2)benzothiazin-10-one, corresponds to the formula:

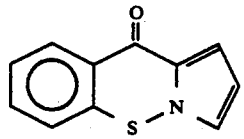

and may be prepared by the following general reaction sequence:

In a first step, 2-(2-ethylthio)benzoyl pyrrole is prepared by reacting ethyl 2-(ethylthio)benzoate and chloromagnesium pyrrole. See, for example, the general procedure of K. C. Nicolaou et al., *J. Org. Chem.*, 1985, 50, p. 1440–1456. The ethyl 2-(ethylthio)benzoate reactant is known in the art and can be prepared by procedures such as taught in S. Oae and T. Numata, *Tetrahedron*, 1974, 30, 2641–2646. The synthesis of chloromagnesium pyrrole is also straightforward and is described in K. C. Nicolaou et al., *J. Org. Chem.*, 1985, 50, p. 1440–1456.

In the second step, the 2-(2-ethylthio)benzoyl pyrrole product is oxidized, for example, with $NaIO_4$ in methanol, to 2-(2-ethylsulfinyl)benzoyl pyrrole.

In the third step, the desired pyrrolo-(1,2-b)-(1,2)benzothiazin-10-one compound is prepared by refluxing the 2-(2-ethylsulfinyl)benzoyl pyrrole with dimethylaminopyridine or triethylamine and toluene.

The following examples illustrate the present invention and the manner by which it can be practiced but, as such, should not be construed as limitations upon the overall scope of the same.

EXAMPLE I

Step 1: Preparation of 2-2(ethylthio)benzoyl pyrrole

Methylmagnesium chloride solution (42 mL of 3 M solution in tetrahydrofuran, 0.1255 mol, 2.2 eq) is added in a slow stream to stirred toluene (165 mL) at 0° C. under nitrogen. To this cold mixture, pyrrole (8.42 g, 0.1255 mole, 2.2 eq) is carefully added dropwise over 10 minutes under nitrogen. After warming to room temperature, the solution is heated at 55° C. for 50 minutes, at which time a solution of ethyl 2-(ethylthio)benzoate (12 g, 0.057 mol) in toluene (18 mL) is added dropwise under nitrogen. The reaction mixture is refluxed for 12 hours. After cooling to room temperature, the reaction is quenched by the addition of saturated $NH_4Cl$ solution (225 mL), diluted with $CH_2Cl_2$ (400 mL), and acidified to pH 3 with 10 percent HCl solution. After separating the layers, the aqueous layer is extracted (3 extractions of 200 mL each) with $CH_2Cl_2$, and the combined organics are washed with water (3 extractions of 300 mL each) and dried with $Na_2SO_4$. After removing the solvent in vacuo, the resulting 13.77 g of crude black oily solid is flash chromatographed with $CHCl_3$ to yield 14.15 g of dark brown solid. After recrystallization with EtOAc and hexanes, 8.07 g (61 percent of theoretical) of tan solid was obtained: mp 79–80° C.

Step 2: Preparation of 2-(2-ethylsulfinyl) benzoyl pyrrole

To a stirred solution of 2-2(ethylthio)benzoyl pyrrole (10 g, 0.043 mol) in $CH_2Cl_2$ (70 mL) and MeOH (100 mL) is added, all at once, a solution of $NaIO_4$ in $H_2O$ (72 mL). The mixture is stirred at room temperature for 18 hours. After vacuum filtration and rinsing of the filter cake with fresh portions of $CH_2Cl_2$, about 100 mL $H_2O$ is added to the mixture and the layers are separated. The aqueous layer is extracted twice with $CH_2Cl_2$ and the combined organics are washed with $H_2O$. After drying with $Na_2SO_4$, the solvent is removed, in vacuo, to give 10.5 g of gold solid. Chromatography yielded 7.26 g of an off-white solid (mp 155–159° C.). This compound is used without further purification in subsequent reactions. An analytically pure sample (mp 160–161° C.) is obtained by recrystallization from EtOAc and EtOH.

Step 3 Preparation of the Pyrrolo(1,2-b)-(1,2)benzo-thiazin-10-one product

Dimethylaminopyridine (0.123 g, 1 mmol, 0.1 eq), 2-(2-ethylsulfinyl)benzoyl pyrrole (2.5 g, 10.1 mmol) and toluene (115 mL) are combined and refluxed with stirring in a flask covered with foil (to exclude light) for 29 hours, at which time the solvent is removed, in vacuo. The resulting crude solid is chromatographed to give 110 mg of comprising pyrrolo(2,1-b)-(1,3)benzo-thiazin-9-one (20 percent), 514 mg of pyrrolo(1,2-b)-(1,2)benzo-thiazin-10-one (46 percent) and 1.11 g of unreacted starting material. A small amount of 1H, 9H-(1)benzothiopyrano(3,2-b)pyrrol-9-one is detected by thin-layer chromatography but was not isolated. The pyrrolo(1,2-b)-(1,2)benzothiazin-10-one is recrystallized with EtOAc and hexanes to give an analytically pure yellow-orange solid (mp 100–102° C.).

The structure identity of the product is confirmed by proton nuclear magnetic resonance spectroscopy ($^1H$), carbon nuclear magnetic resonance spectroscopy (NMR), infrared spectroscopy (IR) and mass spectrometry (MS).

EXAMPLE 2

Alternate Synthesis of Pyrrolo(1,2-b)-(1,2)benzothiazin-10-one

Triethylamine (0.017 mL, 0.12 mmol, 0.1 eq), 2-(2-ethylsulfinyl) benzoyl pyrrole (0.3 g, 1.2 mmol), and toluene (15 mL) are combined and refluxed with stirring for 24 hours. After removal of volatiles in vacuo, a light brown oil is obtained which solidifies to a dark gold solid. Chromatography of the crude solid with a 1:1 ratio of $CHCl_3$ to hexanes yields a product mix comprising 24 mg (0.12 mmol, 15 percent) of pyrrolo(2,1-b)-(1,3)benzothiazin-9-one, 114 mg (0.57 mmol, 69 percent) of pyrrolo(2,1-b)-(1,2)benzothiazin-10-one and 115 mg of light brown solid which proves by NMR to be a mixture of recovered starting material and 1H, 9H-(1)benzothiopyrano(3,2-b)pyrrol-9-one. By integration, the following approximate amounts for the above mixture are calculated: 93 mg (0.38 mmol) and 22 mg (0.11 mmol, 13 percent), respectively.

Antimicrobial Activity

The compound of this invention is useful as an antimicrobial additive to industrial products such as styrene-butadiene latexes used for paper coatings, paints, inks, adhesives, soaps, cutting oils, textiles, and paper and pigment slurries. The compound is also useful as an antimicrobial additive in personal care products such as hand creams, lotions, shampoos, and hand soaps. A further advantage of this invention is its cost-effectiveness for applications which need to have an antimicrobial continuously replenished, such as in cooling towers and pulp and paper mills.

As appreciated in the art, the compound disclosed herein is not necessarily active at the same concentration against different microbial species. That is, there is some species-to-species variation in antimicrobial potency and spectrum of antimicrobial activity.

The present invention is also directed to a method for inhibiting microorganisms which comprises contacting said microorganisms or habitat thereof with an effective amount of the compound of this invention.

The antimicrobial compound of this invention may be added directly to aqueous formulations susceptible to microbial growth, either undiluted or dissolved in inert diluents such as organic solvents such as glycols, alcohols, or acetone. The compound may also be added alone or in combination with other preservatives.

As used herein, the term "microorganism" is meant to refer to bacteria, fungi, viruses, algae, subviral agents and protozoa.

As used herein, the term "antimicrobially-effective amount" refers to that amount of the compound, or of a composition comprising such compound, of this invention needed to exhibit inhibition of selected microorganisms. Typically, this amount varies from providing about 1 part per million (ppm) to about 5,000 ppm by weight of the compound to a microbial habitat being contacted with the compound. Such amounts typically vary depending upon the particular microorganism treated. Also, the exact concentration of the compound to be added in the treatment of industrial and consumer formulations may vary within a product type depending upon the components of the formulation. A preferred effective amount of the compound is from about 1 ppm to about 500 ppm, more preferably from about 1 ppm to about 50 ppm by weight, of a microbial habitat.

The term "microbial habitat" refers to a place or type of site where a microorganism naturally or normally lives or grows. Typically, such a microbial habitat will be an area that comprises a moisture, nutrient, and/or an oxygen source such as, for example, a cooling water tower or an air washing system.

The terms "inhibition", "inhibit" or "inhibiting" refer to the suppression, stasis, kill, or any other interference with the normal life processes of microorganisms that is adverse to such microorganisms, so as to destroy or irreversibly inactivate existing microorganisms and/or prevent or control their future growth and reproduction.

The antimicrobial activity of the compounds of the present invention is demonstrated by the following techniques.

The minimum inhibitory concentration (MIC) for the compound of this invention is determined for 9 bacteria, using nutrient agar, and 7 yeast and fungi, using malt yeast agar. A one percent solution of the test compound is prepared in a mixture of acetone and water. Nutrient agar is prepared at pH 6.8, representing a neutral medium, and at pH 8.2, representing an alkaline medium. The nutrient agars are prepared by adding 23 g of nutrient agar to one-liter of deionized water. In addition, the alkaline medium is prepared by adjusting a 0.04 M solution of N-[tris-(hydroxymethyl)methyl]glycine buffered deionized water with concentrated sodium hydroxide to a pH of 8.5. Malt yeast agar is prepared by adding 3 g yeast extract and 45 g malt agar per liter of deionized water. The specific agar is dispensed in 30 ml aliquots into 25×200 mm test tubes, capped and autoclaved for 15 minutes at 121° C. The test tubes containing the agar are cooled in a water bath until the temperature of the agar is 48° C. Then, an appropriate amount of the one percent solution of the test compound is added (except in the controls where no compound is added) to the respective test tubes so that the final concentrations are 500, 250, 100, 50, 25, 10, 5, 2.5, 1.0 and zero parts per million of the test compound in the agar, thus having a known concentration of test compound dispersed therein. The contents of the test tubes are then transferred to respective petri plates. After drying for 24 hours, the petri plates containing nutrient agar are inoculated with bacteria and those containing malt yeast agar are inoculated with yeast and fungi.

The inoculation with bacteria is accomplished by using the following procedure. Twenty-four hour cultures of each of the bacteria are prepared by incubating the respective bacteria in tubes containing nutrient broth for 24 hours at 30° C. in a shaker. Dilutions of each of the 24 hour cultures are made so that nine separate suspensions (one for each of the nine test bacteria) are made, each containing $10^8$ colony forming units (CFU) per ml of suspension of a particular bacteria. Aliquots of 0.3 ml of each of the bacterial suspensions are used to fill the individual wells of Steer's Replicator. For each microbial suspension, 0.3 ml was used to fill three wells (i.e., three wells of 0.3 ml each) so that for the nine different bacteria, 27 wells are filled. The Steer's Replicator is then used to inoculate both the neutral and alkaline pH nutrient agar petri plates.

The inoculated petri plates are incubated at 30° C. for 48 hours and then read to determine if the test compound which is incorporated into the agar prevented growth of the respective bacteria.

The inoculation with the yeast and fungi is accomplished as follows. Cultures of yeast and fungi are incubated for seven days on malt yeast agar at 30° C. These cultures are used to prepare suspensions by the following procedure. A suspension of each organism is prepared by adding 10 ml of sterile saline and 10 microliters of octylphenoxy polyethoxy ethanol to the agar slant of yeast or fungi. The sterile saline/octylphenoxy polyethoxy ethanol solution is then agitated with a sterile swab to suspend the microorganism grown on the slant. Each resulting suspension is diluted into sterile saline (1 part suspension: 9 parts sterile saline). Aliquots of these dilutions are placed in individual wells of Steer's Replicator and petri plates inoculated as previously described. The petri plates are incubated at 30° C. and read after 48 for yeast and 72 hours for fungi.

Table I lists the bacteria, yeast and fungi used in the MIC test described above along with their respective American Type Culture Collection (ATCC) identification numbers.

TABLE I

| Organisms Used in the Minimum Inhibitory Concentration Test | |
|---|---|
| Organism | ATCC No. |
| Bacteria | |
| Bacillus subtilis (Bs) | 8473 |
| Enterobacter aerogenes (Ea) | 13048 |
| Escherichia coli (Ec) | 11229 |
| Klebsiella pneumoniae (Kp) | 8308 |
| Proteus vulgaris (Pv) | 881 |
| Pseudomonas aeruginosa (Pa) | 10145 |
| Pseudomonas aeruginosa (PRD-10) | 15442 |
| Salmonella choleraesuis (Sc) | 10708 |
| Staphylococcus aureus (Sa) | 6538 |
| Yeast/Fungi | |
| Aspergillus niger (An) | 16404 |
| Candida albicans (Ca) | 10231 |
| Penicillium chrysogenum (Pc) | 9480 |
| Saccharomyces cerevisiae (Sc) | 4105 |
| Trichoderma viride (Tv) | 8678 |
| Aureobasidium pullulan (Ap) | 16622 |
| Fusarium oxysporum (Fo) | 48112 |

In Tables II and III, the MIC values of the compound of this invention as compared to the MIC of a standard commercial preservative with 1-(3-chloroallyl)-3,5,7-triaza-1-azoniaadamantane chloride as the active agent and referred to in Tables II and III as "STANDARD") are set forth for the bacteria organisms and yeast/fungi organisms which are listed in Table I.

TABLE II

| | Minimum Inhibitory Concentrations (in ppm) for Test Compounds in Bacteria Species | | | | | | | | |
|---|---|---|---|---|---|---|---|---|---|
| | ORGANISMS | | | | | | | | |
| Compound | Bs | Ea | Ec | Kp | Pv | PRD | Pa | Sc | Sa |
| STANDARD | | | | | | | | | |
| pH 6.8 | 50 | 100 | 100 | 50 | 50 | 100 | 100 | 50 | 100 |
| pH 8.2 | 250 | 250 | 250 | 250 | 250 | 500 | >500 | 100 | 250 |
| Pyrrolo-(1,2-b)-(1,2)-benzothiazin-10-one | | | | | | | | | |
| pH 6.8 | >10 | 50 | 25 | 25 | 25 | 250 | 250 | 25 | 25 |
| pH 8.2 | 250 | >500 | >500 | >500 | >500 | >500 | >500 | >500 | 500 |

TABLE III

| | Minimum Inhibitory Concentrations for Test Compounds in Yeast/Fungi Species (in ppm) | | | | | | |
|---|---|---|---|---|---|---|---|
| | ORGANISMS | | | | | | |
| COMPOUND | An | Ca | Pc | Sc | Tv | Ap | Fo |
| STANDARD | >500 | >500 | >500 | 500 | >500 | >500 | >500 |
| Pyrrolo-(1,2-b)-(1,2)-benzothiazin-10-one | <10 | <10 | 25 | <10 | 25 | <10 | <10 |

What is claimed is:

1. Pyrrolo-(1,2-b)-(1,2)-benzothiazin-10-one which corresponds to the formula:

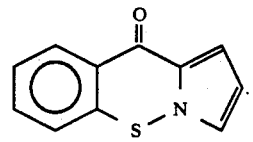

2. An antimicrobial composition comprising an antimicrobially-effective amount of the compound pyrrolo-(1,2-b)-(1,2)-benzothiazin-10-one, as the active material, in intimate admixture with an inert diluent.

3. The composition of claim 2 wherein the compound is present in the composition in an amount sufficient to provide from about 1 part per million to about 5,000 parts per million by weight of the compound to a microbial habitat that is contacted with the composition.

4. A method for inhibiting microorganisms in a microbial habitat which comprises contacting said microbial habitat with an antimicrobial composition comprising an antimicrobially-effective amount of the compound pyrrolo-(1,2-b)-(1,2)-benzothiazin-10-one, as the active material, in intimate admixture with an inert diluent.

5. The method of claim 4 wherein the compound is present in the composition in an amount sufficient to provide from about 1 part per million to about 5,000 parts per million by weight of the compound to the microbial habitat.

* * * * *